(12) United States Patent
Bouchoux et al.

(10) Patent No.: US 12,048,585 B2
(45) Date of Patent: Jul. 30, 2024

(54) ACOUSTIC WINDOW FOR IMAGING AND/OR TREATMENT OF BRAIN TISSUE

(71) Applicant: CARTHERA, Paris (FR)

(72) Inventors: Guillaume Bouchoux, Villeurbanne (FR); Guillaume Godefroy, Brunoy (FR)

(73) Assignee: CARTHERA, Paris (FR)

(*) Notice: Subject to any disclaimer, the term of this patent is extended or adjusted under 35 U.S.C. 154(b) by 468 days.

(21) Appl. No.: 17/298,247

(22) PCT Filed: Nov. 29, 2019

(86) PCT No.: PCT/EP2019/083023
§ 371 (c)(1),
(2) Date: May 28, 2021

(87) PCT Pub. No.: WO2020/109527
PCT Pub. Date: Jun. 4, 2020

(65) Prior Publication Data
US 2022/0110607 A1 Apr. 14, 2022

(30) Foreign Application Priority Data
Nov. 30, 2018 (FR) ..................................... 1872187

(51) Int. Cl.
A61B 8/00 (2006.01)
A61F 2/28 (2006.01)
(Continued)

(52) U.S. Cl.
CPC .......... *A61B 8/4281* (2013.01); *A61F 2/2875* (2013.01); *A61B 8/0808* (2013.01);
(Continued)

(58) Field of Classification Search
CPC ............................ A61B 8/4272; A61B 8/4281
See application file for complete search history.

(56) References Cited

U.S. PATENT DOCUMENTS 5,390,675 A 2/1995 Sheehan et al.
5,468,242 A 11/1995 Reisberg
(Continued)

FOREIGN PATENT DOCUMENTS

EP 2539021 B1 2/2016
KR 101143645 B1 5/2012
(Continued)

OTHER PUBLICATIONS

Carpentier et al., "Clinical Trial of blood-brain barrier disruption by pulsed ultrasound", Science Translational Medicine, vol. 8, Issue 343, Jun. 15, 2016.
(Continued)

*Primary Examiner* — Colin T. Sakamoto
*Assistant Examiner* — Tommy T Ly
(74) *Attorney, Agent, or Firm* — BCF LLP

(57) ABSTRACT

The present invention relates to an acoustic window (1) suitable for implantation at an opening in a patient's skull (4), said acoustic window (1) being intended to cooperate with an external ultrasound probe (2) for the emission of ultrasound waves through the acoustic window (1), remarkable in that the acoustic window comprises a plate (11) including a plurality of through-holes (12), the distance (P) of the through-holes (12) being less than twice the wavelength of the ultrasound waves emitted by the external ultrasound probe (2).

35 Claims, 5 Drawing Sheets

(51) Int. Cl.
*A61N 7/00* (2006.01)
*A61B 8/08* (2006.01)
*A61F 2/30* (2006.01)
*A61M 37/00* (2006.01)

(52) U.S. Cl.
CPC ............ *A61F 2002/30578* (2013.01); *A61F 2310/00023* (2013.01); *A61F 2310/00437* (2013.01); *A61M 37/0092* (2013.01); *A61N 7/00* (2013.01)

(56) References Cited

U.S. PATENT DOCUMENTS

| | | | |
|---|---|---|---|
| 5,743,913 | A | 4/1998 | Wellisz |
| 5,752,515 | A | 5/1998 | Jolesz et al. |
| 5,980,540 | A | 11/1999 | Bruce |
| 6,353,576 | B1 | 3/2002 | Garlick et al. |
| 6,438,238 | B1* | 8/2002 | Callahan ............ A61B 5/6843 |
| | | | D24/134 |
| 6,468,219 | B1 | 10/2002 | Njemanze |
| 6,514,221 | B2 | 2/2003 | Hynynen et al. |
| 6,650,935 | B1 | 11/2003 | Watmough |
| 6,719,449 | B1 | 4/2004 | Laugharn et al. |
| 7,101,337 | B2 | 9/2006 | Aubry et al. |
| 7,655,047 | B2 | 2/2010 | Swords |
| 7,674,229 | B2 | 3/2010 | Hynynen et al. |
| 7,896,821 | B1 | 3/2011 | Magnin et al. |
| 8,155,725 | B2 | 4/2012 | Pernot et al. |
| 8,182,540 | B2 | 5/2012 | Lin et al. |
| 8,226,538 | B2 | 7/2012 | Liu et al. |
| 8,310,132 | B2 | 11/2012 | Martin et al. |
| 8,649,242 | B2 | 2/2014 | Martin et al. |
| 8,840,556 | B2 | 9/2014 | Lin et al. |
| 9,358,023 | B2 | 6/2016 | Konofagou et al. |
| 9,549,819 | B1 | 1/2017 | Bravo et al. |
| 2005/0149032 | A1 | 7/2005 | Vaughen et al. |
| 2006/0235303 | A1 | 10/2006 | Vaezy et al. |
| 2007/0038100 | A1 | 2/2007 | Nita |
| 2008/0009872 | A1 | 1/2008 | Vaughen et al. |
| 2008/0319375 | A1 | 12/2008 | Hardy |
| 2009/0005711 | A1 | 1/2009 | Konofagou et al. |
| 2009/0112278 | A1 | 4/2009 | Wingeier et al. |
| 2010/0094179 | A1 | 4/2010 | Pounder et al. |
| 2010/0143241 | A1 | 6/2010 | Johnson et al. |
| 2010/0222715 | A1 | 9/2010 | Nita |
| 2011/0178441 | A1 | 7/2011 | Tyler |
| 2012/0108976 | A1* | 5/2012 | Salomir ............ A61N 7/02 |
| | | | 600/459 |
| 2013/0079682 | A1 | 3/2013 | Mischelevich |
| 2013/0289411 | A1 | 10/2013 | Barnard et al. |
| 2013/0331685 | A1 | 12/2013 | Liu et al. |
| 2014/0114216 | A1 | 4/2014 | Konofagou et al. |
| 2014/0330123 | A1 | 11/2014 | Manwaring et al. |
| 2015/0065871 | A1 | 3/2015 | Konofagou et al. |
| 2015/0105806 | A1 | 4/2015 | Dorafshr et al. |
| 2015/0196253 | A1 | 7/2015 | Mayer et al. |
| 2015/0321026 | A1 | 11/2015 | Branson et al. |
| 2016/0022308 | A1* | 1/2016 | Rohling ............ A61M 5/46 |
| | | | 604/117 |
| 2016/0074678 | A1 | 3/2016 | Konofagou et al. |
| 2016/0339243 | A1 | 11/2016 | Wingeier et al. |
| 2018/0177487 | A1 | 6/2018 | Deffieux et al. |
| 2020/0138580 | A1* | 5/2020 | Carpentier ............ A61N 7/00 |

FOREIGN PATENT DOCUMENTS

| | | |
|---|---|---|
| WO | 89/07907 A1 | 9/1989 |
| WO | 2004/093725 A2 | 11/2007 |
| WO | 2009/029141 A2 | 3/2009 |
| WO | 2011/029208 A1 | 3/2011 |
| WO | 2014/060914 A1 | 4/2014 |
| WO | 2014/136016 A1 | 9/2014 |
| WO | 2015/075603 A1 | 5/2015 |
| WO | 2016/202955 A1 | 12/2016 |
| WO | 2018/234280 A1 | 12/2018 |
| WO | 2018/234282 A1 | 12/2018 |

OTHER PUBLICATIONS

Carretero-Palacios et al., "Broadband and broadangle extraordinary acoustic transmission through subwavelength apertures surrounded by fluids", New Journal of Physics, 16 (2014).

Chan et al., "Finite Element Modeling of Binary Acoustic Fresnel Lenses", Review of Progress in Quantitative Nondestructive Evaluation, vol. 14, Edited by D.O. Thompson and D.E. Chimenti, Plenum Press, New York, 1995.

Damestani et al., "Transparent nanocrystalline yttria-stabilized-zirconia calvarium prosthesis", Nanomedecine: NBM 2013, pp. 1-4, http://dx.doi.org/10.1016/j.nano.2013.08.002.

Estrada et al., "Extraordinary Sound Screening in Perforated Plates", Physical Review Letters 101, 084302—Published Aug. 2008.

Estrada et al., "Influence of the hole filling fraction on the ultrasonic transmission through plates with subwavelength aperture arrays", Applied Physics Letters 93, 011907 (2008).

Estrada et al., "Angle-Dependent Ultrasonic Transmission Through Plates with Subwavelength Hole Arrays", Physical Review Letters 102, 144301—May 2009.

Estrada et al., "Sound transmission through perforated plates with subwavelength hole arrays: A rigid-solid model", Wave Motion 48, 2011, pp. 235-242.

Estrada et al., "Ultrasonic transmission through multiple-sublattice subwavelength holes arrays", Ultrasonic 52, 2012, pp. 412-416.

Folds et al., "Transmission and reflection of ultrasonic waves in layered media", The Journal of the Acoustical Society of America, vol. 62, No. 5, Nov. 1977.

Gutierrez et al., "Novel Cranial Implants of Yttria-Stabilized Zirconia as acoustic Windows for Ultrasonic Brain Therapy", Advanced Healthcare Materials, vol. 6, Issue 21, 1700214—Published Aug. 2, 2017.

Hao et al., "Resonant transmission of acoustic waves through an elastic plate quasiperiodically corrugated on surfaces", Physics Letters A 375(45), 2011, pp. 4081-4084.

Jones et al., "Three-dimensional transcranial microbubble imaging for guiding volumetric ultrasound-mediated blood-brain barrier opening", Theranostics, 2018, vol. 8, Issue 11, pp. 2909-2926.

Liu et al., "Resonant acoustic transmission through compound subwavelength hole arrays: the role of phase resonances", Journal of Physics Condensed Matter 21 (2009).

Liu et al., "Acoustic transmission resonance and suppression through double-layer subwavelength hole arrays", Journal of Physics Condensed Matter 22(30), 305003—(2010).

Lu et al., "Extraordinary Acoustic Transmission through a 1D Grating with Very Narrow Apertures", Physical Review Letters 99(17), 174301—(2007).

Michaud et al., "Design parameters of stainless steel plates for maximizing high frequency ultrasound wave transmission", Ultrasonics Sonochemistry 26, 2015, pp. 56-63.

Porto et al., "Transmission Resonances on Metallic Gratings with Very Narrow Slits", Physical Review Letters, vol. 33, No. 17, Oct. 4, 1999.

Quadri et al., "High-intensity focused ultrasound: past, present, and future in neurosurgery", Neurosurgery Focus 44(2):E16, Feb. 2018.

Rubio et al., "Pinhole Zone Plate Lens for Ultrasound Focusing", Sensors 2017, 17, 1690.

Smith et al., "Modeling 1-3 Composite Piezoelectrics: Thickness-Mode Oscillations", IEEE Transactions on Ultrasonics, Ferroelectrics, and Frequency Control, vol. 38, No. 1, Jan. 1991.

Tobias et al., "An ultrasound window to perform scanned, focused ultrasound hyperthermia treatment of brain tumors", Medical Physics 14, 228 (1987).

Zhou et al., "Complete transmission through a periodically perforated rigid slab", Journal Acoustical Society of America, vol. 121, No. 6, Jun. 2007.

\* cited by examiner

ACOUSTIC WINDOW FOR IMAGING AND/OR TREATMENT OF BRAIN TISSUE

CROSS-REFERENCE TO RELATED APPLICATIONS

This application is a national phase filing under 35 U.S.C. § 371 of International Application No. PCT/EP2019/083023 filed on Nov. 29, 2019, which claims benefit of priority from French Patent Application No. 1872187 filed Nov. 30, 2018, the contents of which are hereby incorporated by reference in their entirety.

FIELD OF THE INVENTION

The present invention relates to the general technical field of ultrasound devices for imaging and/or treating human or animal brain tissue with ultrasound in order to assist a practitioner in establishing a diagnosis and/or in order to treat a disease.

BACKGROUND OF THE INVENTION

1. General Principle

Various techniques for treating or imaging brain tissue are known.

1.1. Treatment

Various techniques for treating brain tissue, in particular by ultrasound, are known.

The document EP 2 539 021, for example, describes an apparatus for treating brain disorders comprising:
- an implantable ultrasound device made of non-ferromagnetic material,
- a remote control unit of the ultrasound device, and
- means of connection between the ultrasound device and the control unit.

The operating principle of this apparatus is as follows. Once the ultrasound device is implanted in the patient's skull, a succession of treatment sessions is given to treat the patient's disease. At each new treatment session, the intracorporeal device is connected to the control unit via the connection means.

Although the apparatus described in EP 2 539 021 allows an efficient treatment of brain disorders, it would be desirable to have an alternative treatment technique allowing the ultrasound waves to be applied from outside the skull so as to simplify the practitioner's work, as it can sometimes be difficult to install the connection means between the ultrasound device and the control unit.

1.2. Imaging

Brain imaging (or neuroimaging) can be used to allow the practitioner to follow the changes in a brain lesion or a brain tumor for diagnostic and/or surgical purposes.

The most commonly used imaging techniques are computed tomography (CT) and magnetic resonance imaging (MRI). Although these techniques are effective, they have their drawbacks. Magnetic resonance imaging is expensive and requires the injection of a contrast medium into the patient.

It is therefore desirable to have an alternative technique to allow brain imaging.

Imaging techniques based on the use of ultrasound waves to image brain tissue are also known. However, these techniques come up against the difficulty of transmitting the ultrasound waves through the patient's skull.

1.3. Combined Use of an Implanted Window and an External Ultrasound Device

To overcome the disadvantages of existing treatment/imaging methods, the combined use of:
- a window implanted in the thickness of a patient's skull, and
- an external ultrasound device capable of generating ultrasound waves, can be considered.

Indeed, such a combination (implanted window/external ultrasound device) seems to have a number of advantages:
- the ultrasound device being non-implantable, it is easier to manufacture and avoids sterility and MRI compatibility problems,
- the ultrasound device can be more complex than what is feasible in the implantable version; for example, an emitter of the ultrasound device can have multiple channels, allowing electronic adaptation of the beam shape to the target,
- once the window is implanted in the patient, the acoustic treatment can be adapted to best counter changes in the disease (treatment of a local relapse zone, for example).

2. Constraints Related to the Combined Use of an Implanted Window and an External Ultrasound Device However, although the combined use of an implanted window and an external ultrasound device is a promising treatment/imaging method, the importance of emitting ultrasound waves through the implanted window at large angles of incidence has not been taken into account.

However, the ability to tilt the ultrasound device relative to the implanted window without modifying the behavior of the implanted window (i.e., without reducing the transmission coefficient of the ultrasound waves and without increasing the heating of the implanted window) is of major importance to allow the treatment/imaging of a large tissue volume.

Thus, the implanted window must meet certain conditions:
- the size of the window must be small (it is not possible to replace the entire skull with an implanted window),
- the absorption, aberrations and reflection of the ultrasound waves by the window must be minimal, regardless of the geometry of the ultrasound waves (focused, divergent or collimated), and in particular for high incidences: indeed, if the window is acoustically transparent (i.e., low absorption, low deformation and low reflection of the ultrasound waves) at high incidences, it is possible to treat a maximum tissue volume by orienting the ultrasound device to emit ultrasound waves at different angles of incidence,
- the mechanical deformation of the window due to pressure on the patient's head must be minimal; in particular, the window must resist a mechanical pressure exerted on it (typically a force of 100 N applied to the center of the plate must generate a deformation of less than 5 mm),
- preferably the window is compatible with MRI (no heating during the examination, no distortion of the images),
- the window must be biocompatible,
- preferably the window allows the transmission/reception of ultrasound imaging waves,
- preferably the thickness of the window should be small.

In the context of the present invention, "high angle of incidence" means angles of incidence comprised between 20° and 60° relative to an incidence normal to the implanted window.

Various windows have already been proposed to address some of these constraints.

The document "*An ultrasound window to perform scanned, focused ultrasound hyperthermia treatments of brain tumors,*" by J. Tobias, K. Hynynen, R. Roemer, N. Guthkelch, S. Fleischer, and J. Shively, Med. Phys. vol. 14, no. 2, pp. 228-234, 1987, is a study of different materials that might constitute an implanted window for the purpose of treating brain tumors by focused ultrasound hyperthermia (FUH). This document teaches the person skilled in the art that a window made of polyethylene has a better transmission of ultrasound waves than windows made of polystyrene, acrylic or polymethyl methacrylate (materials commonly used in craniotomy), and that the implanted window must be of significant thickness in order to have sufficient mechanical strength.

However, in this document, the impact of the angle of incidence on the transmission of the ultrasound waves and the risks related to the heating of the implanted window during the emission of the ultrasound waves have not been considered.

The document "*Novel Cranial Implants of Yttria-Stabilized Zirconia as Acoustic Windows for Ultrasonic Brain Therapy*" by M. I. Gutierrez, E. H. Penilla, L. Leija, A. Vera, J. E. Garay, and G. Aguilar, Adv. Healthc. Mater, vol. 1700214, pp. 1-11, 2017 teaches the skilled person that an implanted window made of ceramic (yttria-stabilized zirconia) provides good acoustic transmission (81%) at a thickness close to $\lambda/2$, with $\lambda$ the wavelength of the ultrasound waves in the implanted window.

However, in this document, the ultrasound waves are emitted only at an incidence normal to the implanted window. Thus, this document does not consider the impact of the angle of incidence on the transmission of the ultrasound waves and the heating of the implanted window.

These studies provide an initial basis for research. Nevertheless, a number of elements remain to be evaluated to allow for combined use of:

an implanted window, and
an external ultrasound device,
to treat/image brain tissue.

Indeed, in view of the various constraints indicated above, an implanted window for maximizing the volume of tissue imaged or treated has not yet been proposed.

An aim of the present invention is to propose an implanted window for imaging or treating a maximum brain volume.

More precisely, an aim of the present invention is to propose a craniotomy window that allows for good acoustic transmission at a wide angle of incidence in order to maximize the volume of tissue imaged or treated.

BRIEF DESCRIPTION OF THE INVENTION

To this end, the invention proposes an acoustic window suitable for implantation at an opening in a patient's skull, said acoustic window being intended to cooperate with an external ultrasound probe for the emission of ultrasound waves through the acoustic window, remarkable in that the acoustic window comprises a plate including a plurality of through-holes, the distance between two adjacent through-holes being less than five times the wavelength of the ultrasound waves emitted by the external ultrasound probe.

In the context of the present invention, "wavelength" means the wavelength in water of the ultrasound waves emitted by the probe.

The fact that the plate has through-holes as defined above allows the acoustic window according to the invention to be acoustically transparent to ultrasound waves, in particular for ultrasound waves emitted at large angles of incidence.

More precisely, the acoustic window according to the invention:

absorbs ultrasound waves very little, which limits the heating of the window and the intermediate tissues (skin) during the emission of the ultrasound waves, reflects ultrasound waves very little, which maximizes the transmission coefficient of the acoustic window, reduces the incident sound pressure, minimizes standing waves between the window and the transmitter, and deforms the beam of ultrasound waves emitted very little.

This acoustic transparency to ultrasound waves is independent of the material used, so that it is possible to consider the use of materials with high acoustic impedance to produce the acoustic window.

Such materials with high acoustic impedance (i.e., greater than $5 \times 10^6$ Pa s/m) generally have better mechanical strength than materials with low acoustic impedance. It is thus possible to reduce the thickness of the acoustic window when it is made of a material with high acoustic impedance.

Furthermore, high-acoustic-impedance materials—such as metals—can be sterilized using all known sterilization methods, in particular by autoclave. It is therefore easier to sterilize an acoustic window when it is made of a high-acoustic-impedance material.

Finally, high-acoustic-impedance materials generally have a higher heat dissipation coefficient than low-acoustic-impedance materials (which are generally thermally insulating). The heat dissipation through the acoustic window is therefore facilitated when it is made of a high-acoustic-impedance material.

Preferred but non-limiting aspects of the present invention are the following:

the material constituting the plate can be a material of high acoustic impedance higher than $5 \times 10^6$ Pa s/m, such as a metal like titanium, for example;

this improves the mechanical strength of the acoustic window, the surface area covered by the through-holes can be greater than or equal to 50%, preferentially greater than or equal to 75%, and even more preferentially greater than or equal to 90% of the total surface area of the plate (11);

this improves the transmission coefficient of the acoustic window, the distance between two adjacent through-holes may be less than twice the wavelength of the ultrasound waves emitted by the external ultrasound probe, preferentially less than 1.7 times the wavelength of the ultrasound waves emitted by the external ultrasound probe, and even more preferentially less than the wavelength of the ultrasound waves emitted by the external ultrasound probe;

this improves the transmission coefficient and the thermal characteristics of the acoustic window, the dimensions of each through-hole may be less than twice the wavelength of the ultrasound waves emitted by the external ultrasound probe, preferentially less than 1.7 times the wavelength of the ultrasound waves emitted by the external ultrasound probe, and even more preferentially less than the wavelength of the ultrasound waves emitted by the external ultrasound probe;

this also improves the transmission coefficient and the thermal characteristics of the acoustic window, the through-holes can be identical in shape;

this improves the homogeneity of the ultrasound wave field transmitted to the brain tissue, and limits the deformation of the transmitted ultrasound wave field, the through-holes can be evenly distributed on the plate;
this improves the homogeneity of the ultrasound wave field transmitted to the brain tissue, and limits the deformation of the transmitted ultrasound wave field, the through-holes can be arranged in a square pattern;
the through-holes can be arranged in a hexagonal pattern;
the hexagonal arrangement increases the ratio between the surface area covered by the through-holes and the total surface area of the plate,
the acoustic window may further comprise at least one layer of polymeric material, such as silicone, containing the plate;
this limits the discomfort caused by the implantation of the acoustic window in the patient's skull and also guarantees the biocompatibility of the acoustic window, makes the acoustic window impermeable, and modifies the mechanical properties of the acoustic window,
the acoustic window may further comprise at least one positioning marker;
this makes it easier to detect the acoustic window once it has been implanted and covered by the skin of the patient's skull,
the acoustic window may further comprise a reinforcing frame extending around the periphery of the plate;
this increases the mechanical strength of the acoustic window.

The invention also relates to a surgical implant set comprising a package, in particular an individual package, an aseptic acoustic window as described above contained in the package, and instructions for use of the window as an acoustic window.

The invention also relates to a system for imaging and/or treating brain tissue, the system including an ultrasound-wave-generating probe and an acoustic window as described above.

The invention also relates to the use of a plate including a plurality of through-holes as an acoustic window of a system for imaging and/or treating brain tissue, said system including:
the acoustic window suitable for implantation at an opening in a patient's skull, and
an ultrasound-wave-generating probe able to cooperate with the acoustic window for the emission of ultrasound waves through the acoustic window,
the plate being such that the distance P between two adjacent through-holes is less than twice the wavelength of the ultrasound waves emitted by the external ultrasound probe.

The invention also relates to a process for imaging and/or treating brain tissue from a system including an ultrasound-wave-generating probe and an acoustic window as described above, the process comprising the steps consisting in:
positioning the probe on the acoustic window,
tilting the probe relative to the acoustic window to emit ultrasound waves through the acoustic window at an angle of incidence comprised between 0 and 60° relative to an angle of incidence normal to the acoustic window, said angle of incidence being in particular greater than 20° (preferentially 30°) relative to the normal angle of incidence.

BRIEF DESCRIPTION OF THE DRAWINGS

Further advantages and features of the invention will emerge from the following description of several alternative embodiments, given by way of non-limiting examples, from the appended drawings wherein.

DETAILED DESCRIPTION OF THE INVENTION

Various examples of systems for imaging and/or treating brain tissue will now be described with reference to the figures. In these various figures, equivalent elements are designated by the same numerical reference.

1. General Principle

Figure 1:
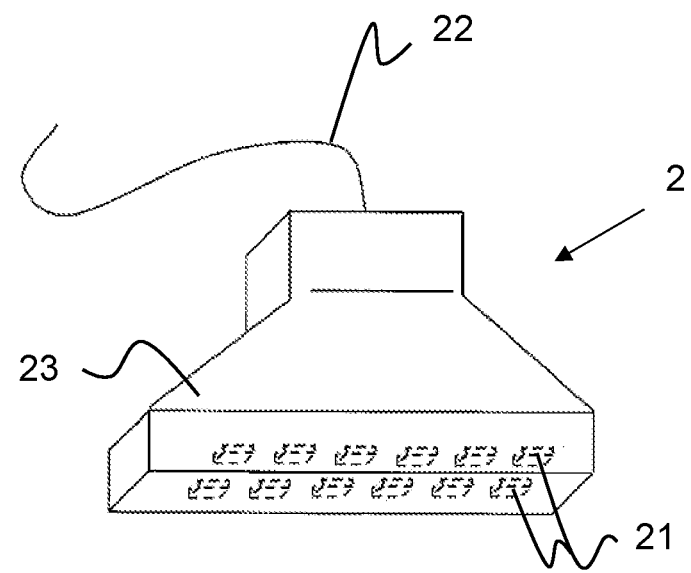
FIG. 1 is a schematic representation of a system including an acoustic window and an acoustic wave emission probe.
Figure 1:
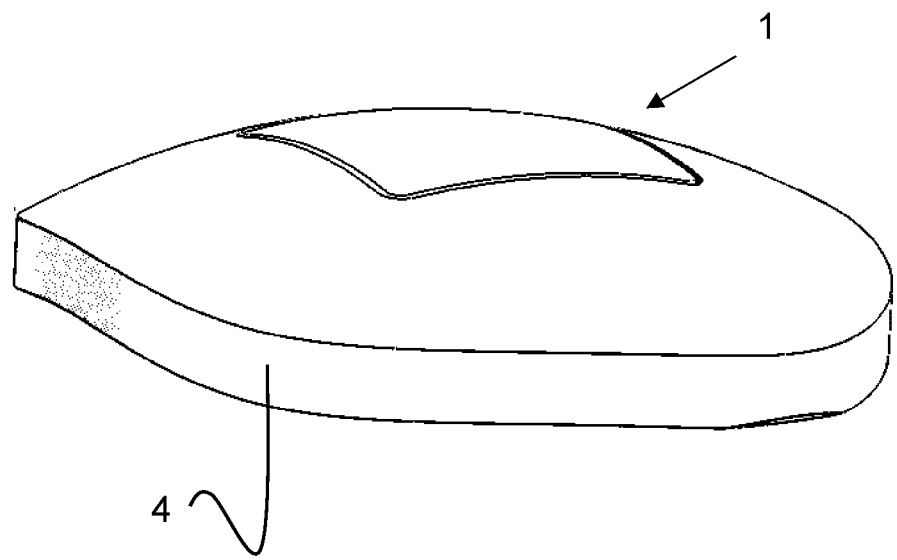

With reference to FIG. 1, a system for imaging and/or treating brain tissue has been schematically illustrated.

The system for imaging and/or treating brain tissue comprises:
An acoustic window 1, and
A probe 2 able to generate ultrasound waves.

This system allows a practitioner to check the change in brain tissue by imaging and/or to treat the brain tissue using ultrasound.

The window 1 is intended to be implanted in the patient, in particular at an opening in the patient's skull 4. This provides protection to the brain and prevents its deformation due to pressure changes. The window can advantageously be sterilized by any technique known to the person skilled in the art (by autoclaving and/or using a gas such as ethylene oxide, and/or by X-ray or gamma irradiation) once the window is packaged. An acoustic window which is packaged in aseptic packaging during manufacture and can therefore be used directly by the surgeon is thus obtained.

The probe 2 is able to be manipulated by the practitioner, or by an automatic displacement system carrying the probe. It comprises a housing 23 in which transducers 21 for generating ultrasound waves are housed. The transducers may be arranged in a linear or matrix array of phased array transducers. Such phased array transducers can be independently controlled to generate acoustic signals with different phases to vary the direction of propagation of the ultrasound waves. The housing is connected to a control device via an electrically conductive cable 22. The probe may also include a coupling element—for example, a gel or pouch containing a liquid such as water—to be positioned between the transducers and the patient to transmit the ultrasound waves between the transducer and the patient.

Such a probe 2 is known to the skilled person and will not be described in greater detail hereinafter. It allows the generation of acoustic waves at frequencies comprised between 200 kHz and 10 MHz, preferably comprised between 500 kHz and 2 MHz.

2. Context

As mentioned above, the implanted window 1 must respect certain conditions, in particular with regard to its dimensions (which are limited), and its ultrasound absorption/reflection rates, which must be minimal.

These constraints make it difficult to maximize the volume of brain tissue that can be imaged/treated.

Figure 2:
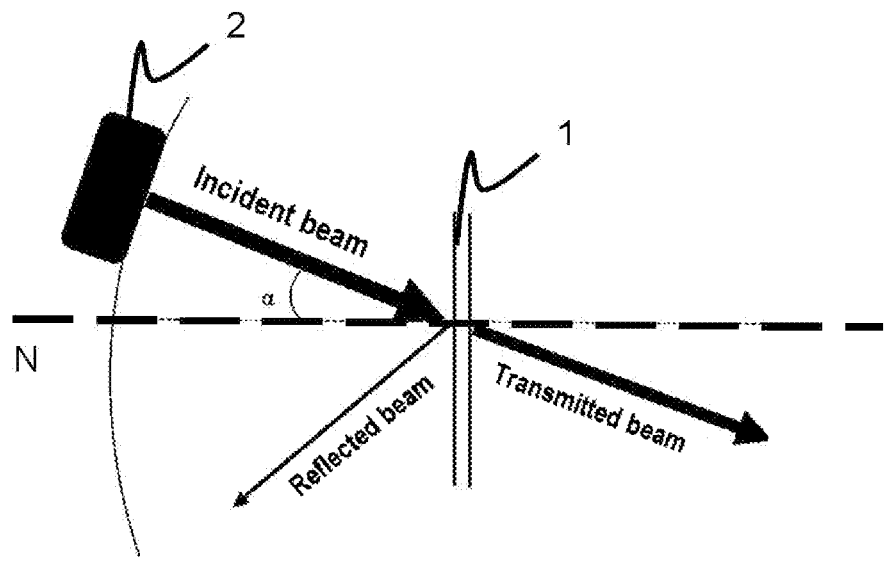
FIG. 2 is a schematic diagram showing the transmission and reflection of a deflected ultrasound wave through an acoustic window.

Indeed, to maximize the volume of brain tissue imaged/treated:
- A first solution may consist in increasing the dimensions of the window 1, and in positioning the probe 2 in front of the window 1 according to a normal angle of incidence N to emit ultrasounds;
- However, the length and width of a window 1 cannot be greater than the maximum length and width limits without compromising the patient's integrity,
- A second solution may consist (as shown in FIG. 2) in tilting the probe 2 about the normal incidence N to emit ultrasound waves at different angles of incidence α;
- However, in this case, the increase in the angle of incidence α generally induces an increase in the reflection of ultrasound by the window 1 and its absorption rate (the thickness of the acoustic window crossed by the ultrasound being lower at normal incidence than at any other angle of incidence). This variation in ultrasound transmission is troublesome in clinical applications because the acoustic field in the brain is not controlled. While the general tendency is that the transmission reduces drastically when approaching the critical angle, it can be higher at non-normal incidence.
- An advantage of the windows according to the invention is that the variation is very small and much better controlled than for plates according to the prior art, which allows a much better control of the pressure applied to the patient's brain whatever the angle of incidence or the shape of the beam. This is essential for our application (opening of the BBB where the pressure in the brain must be as precise as possible).

This is why the inventors have developed a new system for imaging and/or treating brain tissue including a novel window 1 and a probe 2.

3. Acoustic Window

3.1. Definition

In the context of the present invention, "acoustic window" means an implanted window whose amplitude transmission coefficient of the ultrasound waves is greater than 80% for angles of incidence comprised between 0 and 30° with respect to normal incidence.

The amplitude transmission coefficient can be measured using the method described below.

An ultrasonic transmitter (a planar element made of piezocomposite material with a diameter of 10 mm operating at 1 MHz) is used to generate a wave in water. The transmitter is excited by a wave burst (for example 10 sine periods or 10 μs). An ultrasonic receiver (an Onda HNC0200-1168 hydrophone and its Onda AH-2020-20-025-1127_1-20t preamplifier) is immersed in the water in front of the transmitter, in its axis, in the so-called far-field zone, i.e., 5 cm from the transmitter. The precise position of the receiver in the plane normal to the acoustic axis is adjusted to maximize the amplitude of the received signal (positioning can be done with a motorized bench or manually). Once correctly positioned, the receiver is held still during all measurements. The amplitude of the received signal at the frequency of interest is measured with an oscilloscope (i.e., the RMS value excluding transients), which serves as a windowless reference amplitude. The acoustic window is positioned between the transmitter and the receiver. The distance between the transmitter and the acoustic window is of the order of the distance between an implanted window and an extracorporeal transmitter (for example 1 or 2 cm). The angle between the window and the acoustic axis is chosen (angle of incidence of the wave). A new measurement of the amplitude at the receiver is performed. The transmission coefficient is the ratio between the amplitudes read on the oscilloscope with and without window. This method for measuring the acoustic transmission coefficient through a plate is known to the skilled person and many alternatives exist.

Figure 9:
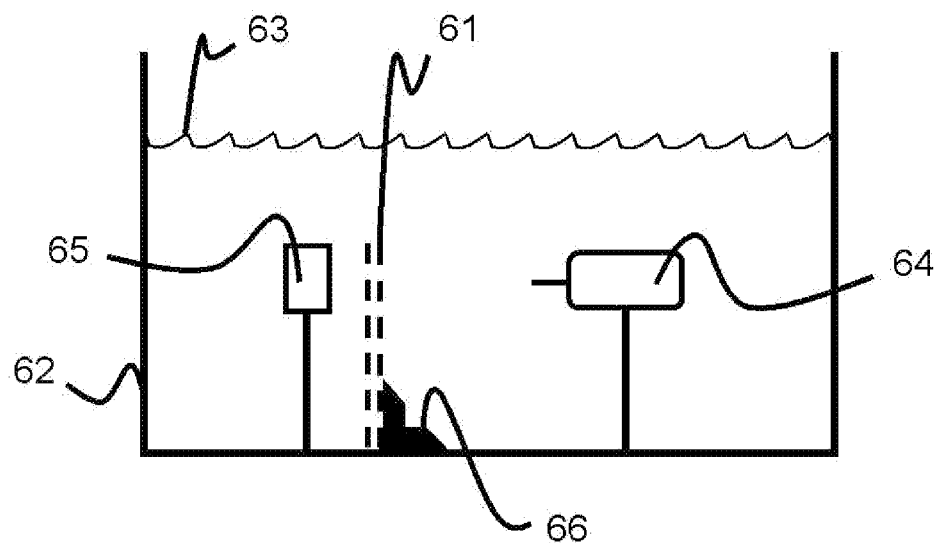
FIG. 9 is a schematic illustration of an arrangement for measuring the transmission coefficient of an acoustic window.

The arrangement used, which is conventional for this type of measurement, is shown in FIG. 9. The plate 61 including the through-holes is placed in a tank 62 filled with water 63 between the hydrophone 64 and the transducer 65. The transducer 65 is a 10 mm diameter flat piezoceramic disk (PZ 26, Ferroperm Piezoceramics) resonating at 1 MHz. It is powered by a CarThera (GEN-00 IGT) generator (not shown). The signal collected by the hydrophone 64 (HYD04) is preamplified then amplified (Onda equipment) then sampled via an oscilloscope (Picoscope 3205D) at a frequency of 250 kHz. Degassed water is used to eliminate the influence of gas bubbles.

A wave of 1 MHz (frequency of interest used clinically for opening the blood-brain barrier) of a duration of 1 μs with a Tr of 20 ms is generated. The signal from the hydrophone is averaged over 50 repetitions to increase the signal-to-noise ratio (SNR). A measurement of the amplitude of the received signal is made without a plate and is used as a reference to calculate the transmission through the plate. A measurement of the amplitude of the received signal is made by positioning the plate on a support 66 between the hydrophone 64 and the transducer 65. The transmission is calculated using the following formula:

$$|T(\omega)| = \frac{|H(\omega)_{plate}|}{|H(\omega)_{ref}|}$$

Where:
- $|H(\omega)_{plate}|$ is the absolute value of the average (averaged over fifty repetitions) of the signal measured by the hydrophone when the plate is placed on the support, and
- $|H(\omega)_{ref}|$ is the absolute value of the average (averaged over fifty repetitions) of the signal measured by the hydrophone when the support 66 is without a plate.

The incidence of the beam is first normal (zero deflection) then it is varied by steps of 10° to 50° to measure the transmission coefficient of the plate for different angles of incidence of the ultrasound waves.

3.2. Structure of the Acoustic Window

Figure 3:
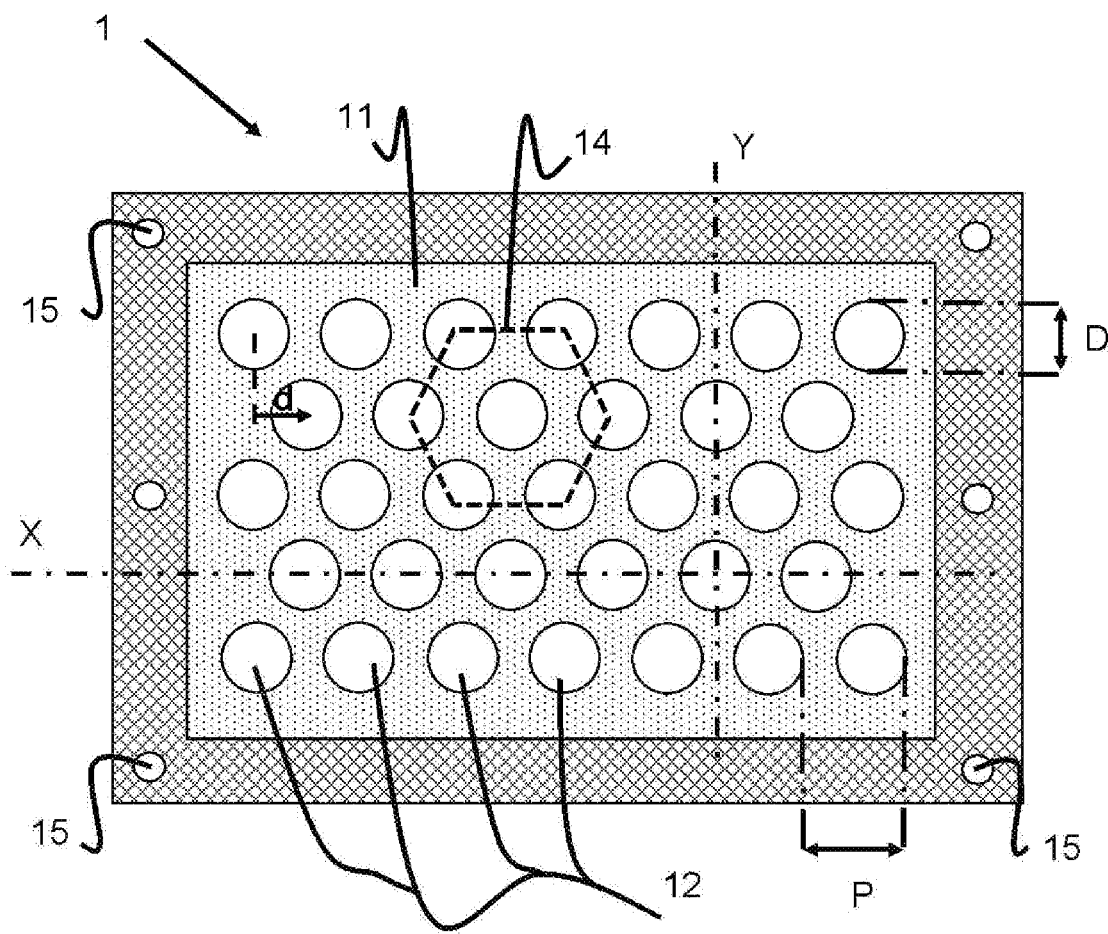
FIGS. 3 to 5 are schematic representations in top view of different alternative embodiments of an acoustic window.
Figure 4:
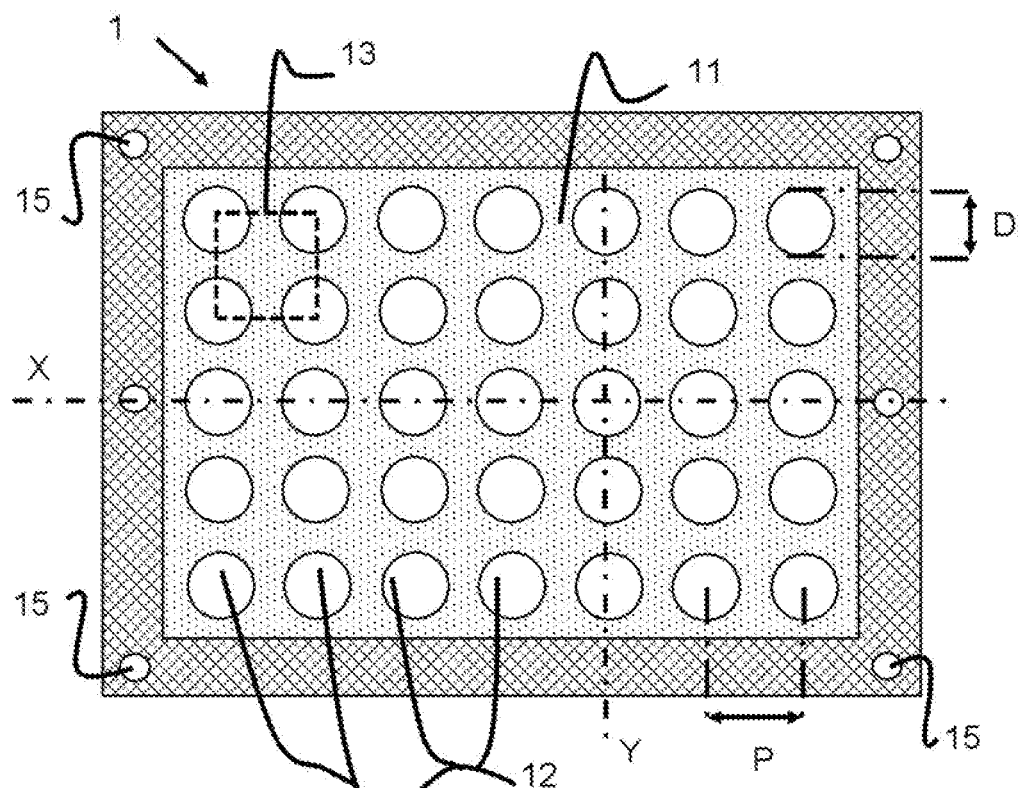
Figure 5:
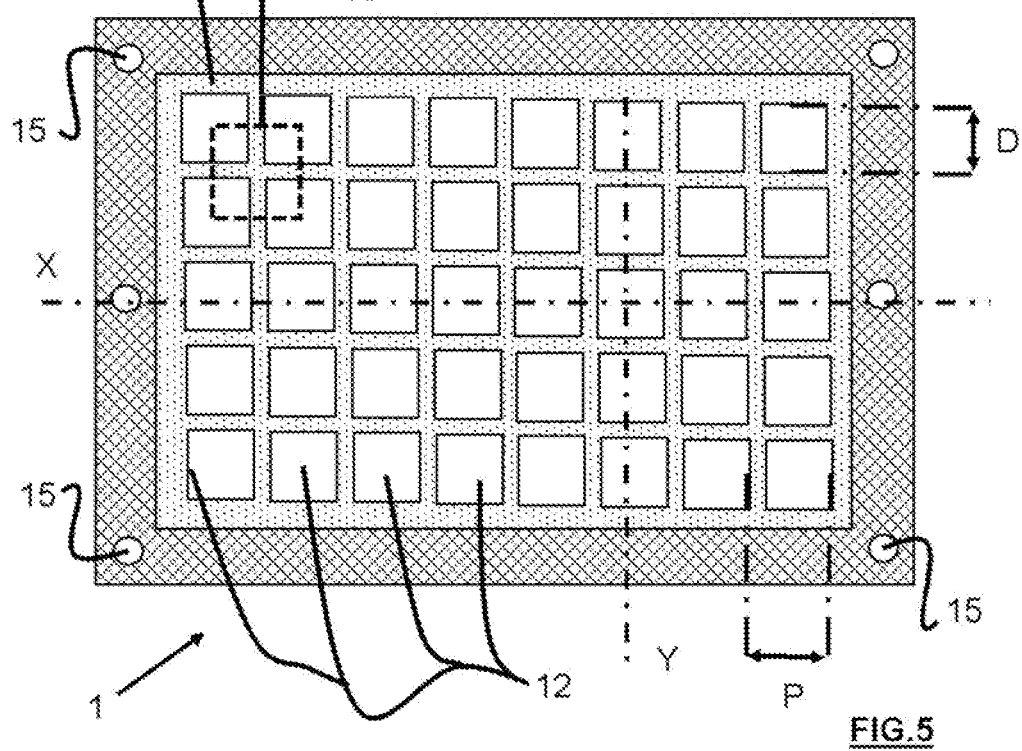

With reference to FIGS. 3 through 5, various examples of an acoustic window 1 used to close an opening in a patient's skull 4 for imaging and/or ultrasound treatment purposes have been illustrated.

The window 1 comprises a plate 11. The plate 1 is generally rectangular, but may have any shape, such as a circular shape. The dimensions of the plate 1 (length and width) can be comprised between 1 and 15 centimeters.

The plate 1 may be substantially flat. Alternatively, the plate 1 may be curved or deformed to follow the curvature of the patient's skull 4.

3.2.1. Through-Holes

One of the novel features of the acoustic window 1 according to the invention is that the plate 11 comprises a plurality of through-holes 12. These through-holes can be obtained by drilling a solid plate, by molding, or by weaving wires—in particular metal wires—in order to form a mesh made up of meshed wires.

Each dimension D (length, width) of each through-hole 12 is preferably less than twice the wavelength (in water) of the ultrasound waves emitted by the probe 2, and preferentially less than 1.7 times the wavelength (in water) of the ultrasound waves emitted by the probe 2. For example, for ultrasound waves emitted at a frequency of 1 MHz, each dimension D of each through-hole 12 is less than 3 millimeters, preferentially less than 2 millimeters.

Furthermore, the distance P between two adjacent through-holes 12 is less than five times, preferentially less than twice the wavelength (in water) of the ultrasound waves emitted by the probe 2, and even more preferentially less than 1.7 times the wavelength (in water) of the ultrasound waves emitted by the probe 2. By way of indication, for ultrasound waves emitted at a frequency of 1 MHz, the distance P between two adjacent through-holes 12 is less than 3 millimeters, preferentially less than 2 millimeters.

In the context of the present invention, "adjacent through-holes" means two adjacent through-holes 12 between which there is no other through-hole. In other words, two through-holes 12 are said to be "adjacent" when the space between said adjacent through-holes is devoid of a through-hole.

In the context of the present invention, "distance between through-holes" means the length separating the beginning (respectively the center or the end) of two successive adjacent holes in a given direction. When the through-holes are arranged in a periodic array, this distance corresponds to a pitch (or period).

A window 1 according to the invention composed of a plate including an array of through-holes 12 of dimensions and distance less than twice the wavelength of the ultrasound waves emitted by the probe 2 has a number of advantages, and in particular:
- good transmission of acoustic waves, in particular at high angles of incidence,
- good thermal characteristics (very efficient heat dissipation due to the high thermal conductivity of metals and the structure with a large surface area for heat exchange).

Advantageously, the distance P between two adjacent through-holes 12 is equal to or less than λ, where λ is the wavelength in water of the ultrasound waves emitted by the probe 2. Still advantageously, P<λ/2. This makes the transmission of the ultrasound waves very regular regardless of the angle of incidence α of the probe 2.

3.2.2. Arrangement of Holes

In the embodiments shown in FIGS. 3 to 5, the through-holes 12 are arranged in an array.

Preferably, the through-holes 12 are evenly distributed over the plate 11 and have an identical shape. This ensures the homogeneity of the ultrasound wave field transmitted to the brain tissue. This also limits the deformation of the ultrasound wave field transmitted to the brain tissue.

However, in certain alternative embodiments, the plate 11 may comprise through-holes 12 of distinct and/or irregularly distributed shapes, depending in particular on the intended application.

In the embodiments shown in FIGS. 4 and 5, the through-holes 12 are arranged in a square arrangement 13 (i.e., "round mesh 90", "square mesh 90"). In other words, the center of each through-hole 12 is:
- aligned with the centers of adjacent holes along a first direction X, and
- aligned with the centers of adjacent holes along a second direction Y perpendicular to the direction X.

In the illustrated embodiment 3, the through-holes 12 are arranged in a hexagonal arrangement 14 (i.e., "mesh 60"). In other words, the center of each hole is:
- aligned with the centers of the adjacent holes along the first direction X, and
- offset (by a non-zero distance "d" in the direction X) from the centers of adjacent holes in the second direction Y perpendicular to the direction X.

The hexagonal arrangement 14 (FIG. 3) has a better transmission coefficient of the ultrasound waves than the square arrangement 13 (FIGS. 4, 5) for the same percentage of holes. Indeed, the hexagonal arrangement increases the ratio between the surface area covered by the through-holes and the total surface area of the plate.

3.2.3. Shape of Through-Holes

The through-holes 12 may be of various shapes. In the embodiments illustrated in FIGS. 3 and 4, the through-holes 12 are round. In the embodiment shown in FIG. 5, the through-holes 12 are square. Of course, the through-holes 12 may have other shapes (triangular, elliptical, pentagonal, hexagonal, honeycomb, diamond, etc.).

The inventors have in fact observed that the shape of the through-holes 12 has no influence on the transmission coefficient of the ultrasound waves, as long as the conditions on the distance between the through-holes is respected (see point 3.1.1.).

An advantage of using round through-holes 12 is that the plate 11 has a better mechanical strength to the shear stresses that can be applied to the window 1 during its implantation.

3.2.4. Material/Hole Ratio

Advantageously, the ratio between the surface area covered by the through-holes 12 divided by the total surface area of the plate 11 is greater than or equal to 50%, preferentially greater than 75%, and even more preferentially greater than or equal to 90%.

Indeed, the transmission coefficient of the ultrasound waves increases when the material to void ratio decreases, i.e., when the surface area of the plate 11 occupied by the material divided by the surface area of the plate occupied by the through-holes decreases.

Thus, as the surface area covered by the through-holes 12 increases in comparison with the surface area covered by the material constituting the plate 11, the transmission of the ultrasound waves is improved.

3.2.5. Plate Thickness

Preferably, the thickness of the plate is less than 1 mm (in particular if the material constituting the plate is a metal).

Indeed, the transmission coefficient of the ultrasound waves increases when the thickness of the plate decreases.

Furthermore, the thickness of the plate is preferentially sufficient to ensure mechanical stiffness. This makes it possible to have a plate 11 which satisfies the minimum deformation criterion which an acoustic window 1 must respect when a mechanical pressure is exerted thereon (typically a force of 100 N applied to the center of the plate must generate a deformation of less than 5 mm).

Thus, by way of indication, the thickness of the plate 11 is preferably comprised between 80 µm and 500 µm.

3.3. Material Constituting the Acoustic Window

The plate 11 is not necessarily made of an acoustically transparent material to allow the passage of ultrasound waves generated by the probe 2 through the acoustic window to treat/image the brain tissue.

In an embodiment, the material constituting the plate is a metal. The use of a metal plate makes it possible to meet the mechanical deformation constraints that the acoustic window must satisfy (i.e., mechanical deformation of less than 2.5 mm in response to a bearing force of 50 newtons applied to the center of the plate).

Preferably, the metal constituting the plate is titanium (or another metal or material, possibly coated with parylene or equivalent if it is not biocompatible per se). The use of titanium has a number of advantages:
- titanium is a material that is well accepted by the bone structure (good biocompatibility), which limits the risk of rejection of the acoustic window after its implantation,
- titanium is a very strong material.

The reader will appreciate that the skilled person considers metals to be unfavorable materials for the transmission of ultrasound, particularly because of their high acoustic impedance.

Indeed, it is known that a metal plate can be relatively transparent to the ultrasounds applied according to a normal incidence to the plate if its thickness is equal to half the wavelength of the emitted ultrasound waves. However, according to the skilled person, such a plate becomes unsuitable to constitute an acoustic window if the ultrasound waves are emitted according to other angles of incidence than the normal incidence (the ultrasound waves crossing then a thickness of plate higher than the half of their wavelength, which strongly attenuates their transmission).

Thus, the use of a metal to constitute the plate 11 of an acoustic window 1 goes against the biases of the skilled person. However, the use of metal has advantages over other materials which are intrinsically transparent to ultrasound, particularly with regard to its mechanical strength.

Of course, the material constituting the plate 11 may be a material other than a metal. In particular, the plate 11 may be made of a polymeric material (such as polyethylene, polystyrene, acrylic, polyetheretherketone (PEEK) or poly(m-ethyl methacrylate) (PMMA)) or a thermoplastic elastomer (such as PEBAX).

3.4. Other Optional Aspects

3.4.1. Reinforcing Frame

As illustrated in FIGS. 3 to 5, the window 1 may also comprise a reinforcing frame extending at the edges of the plate 11. This increases the mechanical strength of the window 1.

The reinforcing frame can consist of rods (or plates) made of a rigid material—such as titanium or stainless steel or any other biocompatible metal known to the skilled person—with a thickness greater than the thickness of the plate 11.

Different solutions can be chosen for the implantation of the window 1 described above in the patient's skull. In particular, the window 1 can be implanted:
- so as to extend into the extension of the patient's skull, or
- so as to extend above the patient's skull.

The window 1 can be attached to the skull 4:
- by gluing, for example using an adhesive—such as cyanoacrylate,
- by screwing, by means of fastening elements—such as bone anchoring screws intended to cooperate with the through-holes 15 in the window 1,
- or by any other means known to the skilled person for attaching the window 1.

3.4.2. Coating

The window 1 may also comprise one or more layer(s) of acoustically transparent material around the plate 11, such as parylene or silicone. More precisely, the plate 11 may be embedded in the layer(s) of material.

Coating the window in such a material limits the discomfort caused by the implantation of the acoustic window in the patient's skull. Indeed, the abrasive character of the plate including the through-holes can cause irritations of the dura mater or of the skin covering the acoustic window.

The coating can have other functions:
- Make the implant biocompatible,
- Make the plate including the through-holes impermeable,
- Modify the mechanical properties of the mesh,
- Avoid injuries due to the edges of the plate, etc.

Without the minimum deformation constraint that the window 1 must satisfy, an ideal material to constitute the plate would be silicone. However, silicone as such is too soft to satisfy this minimum deformation stress. When the plate according to the invention is embedded in a silicone layer, the silicone layer is stiffened while maximizing the ultrasound transmission coefficient of the acoustic window.

3.4.3. Positioning Marker(s)

The window 1 may also comprise one or more positioning marker(s) allowing the practitioner to identify the position of the plate 11 once it is implanted and covered with the skin of the patient's skull.

The use of positioning markers reduces the time required to implement an imaging and/or treatment session of brain tissue, in particular by facilitating the location of the acoustic window and thus the positioning of the probe opposite the window 1 in order to image and/or treat the underlying brain tissue.

Each positioning marker may consist of:
- A mechanical element tactilely locatable by the operator through the patient's skin—such as a pin extending outward from the plate 11, or
- An ultrasonically visible position marker—such as an echogenic metal or plastic structure, or
- A position marker visible by MRI, or
- A position marker which is optically visible, for example in the infrared range.

Each marker may be different and include a code for locating and characterizing the window 1. For example, in an alternative embodiment, each marker comprises a substrate having a first acoustic impedance and an element having a second acoustic impedance. For each marker, the element of second acoustic impedance is buried at a different depth in the substrate so that the distribution of the elements in the substrate provides a code for identifying said marker.

4. Operating Principle

The operating principle of the system for imaging and/or treating brain tissue will now be described with reference to FIG. 9.

In a first step, the practitioner implants (step 100) the window 1 in the patient's skull. He or she makes one (or more) opening(s) in the patient's skull, and attached a window 1 in the opening (or in each respective opening) by bonding or anchoring. When implanting the window, the practitioner may fill the free space between the window 1 and the dura mater with a suitable material (gel or saline solution). The practitioner then covers the window with the patient's skin. Advantageously, the incision in the patient's skin is made in such a way as to avoid the scar resulting from the closure of the skin after implantation of the window covering the window (the quality of transmission of ultrasound waves being reduced through the scars).

Once the window is implanted, a succession of brain tissue imaging and/or treatment sessions can be provided to the patient.

At each new treatment session, the practitioner implements a step of detecting (step 200) the position of the window 1. He or she switches the probe to a locating mode (probe transducers or specific transmitters/receivers activated in ultrasound mode A), applies an ultrasound transmission gel to the patient's hair, and moves the probe over the patient's skull to detect the position of the window 1.

When the window 1 is detected, the processing unit sends information to the practitioner to hold the probe still. Optionally, the probe can be removed to reapply transmission gel to the patient's hair above the window before repositioning (step 300) the probe at the window 1.

Once the probe is positioned, the practitioner orients the probe to emit ultrasound waves in one (or more) direction(s) of interest at different angles of incidence comprised between 0 and 60° with respect to normal incidence (90-30 with respect to grazing incidence).

When the probe is correctly oriented, the practitioner activates the transducers to allow imaging or treatment of the brain tissue (step 400).

5. Theory of the Invention

The transmission performance of an acoustic window 1 according to the invention including a plate having a plurality of through-holes 12 was compared with the transmission performance of an acoustic window including a solid plate.

The acoustic window according to the invention had the following features:

Through-hole shape: round,
Through-hole diameter: D=1 mm,
Distance between through-holes: P=1.7 mm,
Plate thickness: e=0.3 mm,
Through-hole arrangement: hexagonal 14 (60° pattern),
Plate material: titanium.

The acoustic window including a solid plate had the following features:

Solid plate,
Plate thickness: e=1.6 mm,
Plate material: polyetheretherketone (PEEK).

The features chosen for the acoustic window including a solid plate are those which make it possible to obtain the best performance (in terms of transmission of the ultrasound waves) for a solid plate while ensuring adequate mechanical performance.

The probe 2 used emitted ultrasound waves at a frequency of 1 MHz. The transmission coefficients of the two acoustic windows were studied for different inclinations of the probe 2 around normal incidence (tilting angle between 0 and 50° around normal incidence).

Figure 6:
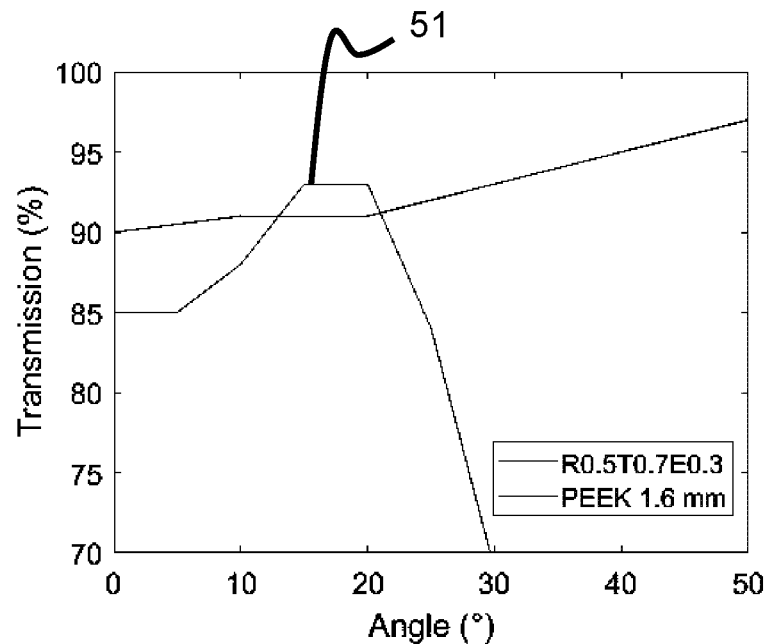
FIGS. 6 and 7 are graphs showing the transmission rate of the ultrasound waves as a function of the angle of incidence of the probe.

The results obtained are shown in FIG. 6, which is a graph representing the transmission rate of the ultrasound waves as a function of the angle of incidence of the probe 2.

As the reader will appreciate in FIG. 6, the acoustic window including a solid plate has good transmission coefficients (>85%) for incidence angles comprised between 0° and 20°. When the angle of incidence of the probe exceeds 20°, the transmission coefficient decreases sharply to become zero when the angle of incidence is substantially equal to 30°.

The acoustic window according to the invention, in turn, has transmission coefficients higher than 90% for all angles of incidence comprised between 0° and 50°. It can also be seen in FIG. 6 that the value of the transmission coefficient obtained with a window according to the invention remains substantially constant regardless of the angle of incidence of the ultrasound waves.

This study highlights the advantage of the window according to the invention (comprising a plate including through-holes) by the stability of the values of transmission coefficients and its very good results for high angles of incidence up to 60° with respect to normal incidence.

Such results were in no way foreseeable for the skilled person for the following reasons. Indeed, to calculate the acoustic impedance of a plate 11 including through-holes 12, the skilled person will consider the "plate+holes" assembly as an average homogeneous material.

This approximation is commonly used, for example in the case of piezocomposite materials (ceramic rods in a lightweight resin matrix). Such an approximation is described in particular in Smith, W. A., and B. A. Auld. "*Modeling 1-3 Composite Piezoelectrics: Thickness-Mode Oscillations*" https://doi.org/10.1109/58.67833 ("Such composites can be treated as a homogeneous medium with new effective material parameters so long as the rod size and spacing are sufficiently fine compared with all relevant acoustic wavelengths").

Considering the "plate+holes" assembly as an average homogeneous material, the skilled person will, for a plate of which 50% of the surface area is covered with through-holes, suppose that the acoustic impedance of the "plate+holes" assembly is equal to the average between the acoustic impedance of water (1.5 MRayl) and the acoustic impedance of the metal (27 MRayl for titanium):

$$I_{equivalent}=(I_{water}+I_{titanium})/2=(1.5+27)/2=14 \text{ MRayl}$$

According to this naive approach, the skilled person will consider that an acoustic window comprising a 300 μm thick plate including through-holes has a transmission coefficient of 50% at 1 MHz.

As shown in FIG. 6, such an acoustic window has transmission coefficients greater than 90% for angles of incidence comprised between 0 and 60° with respect to normal incidence.

Thus, there was no incentive for the person skilled in the art to propose the use of an acoustic window including through-holes in a system for imaging and/or treating brain tissue comprising said window and an ultrasound-wave-generating probe intended to be positioned at the acoustic window.

The results shown in FIG. 6 were obtained by simulation. Experimental measurements of the transmission coefficients of three acoustic windows according to the invention for different angles of incidence were performed (probe 2 emitting ultrasound waves at a frequency of 1 MHz). These experimental measurements were compared with experimental measurements of the transmission coefficients of an acoustic window comprising a solid PEEK plate.

Figure 7:
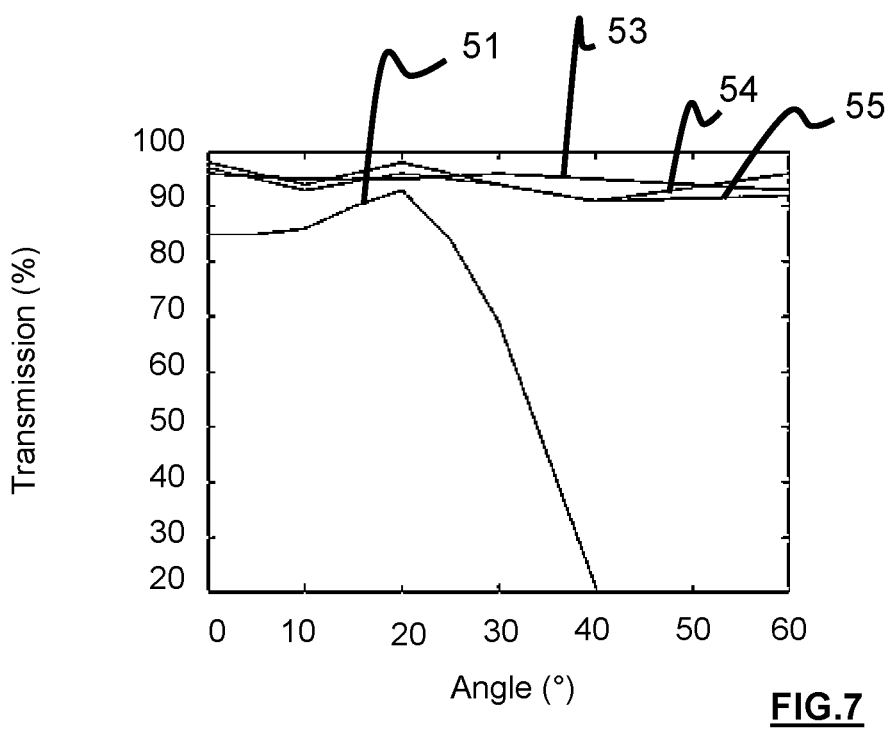
Figure 8:
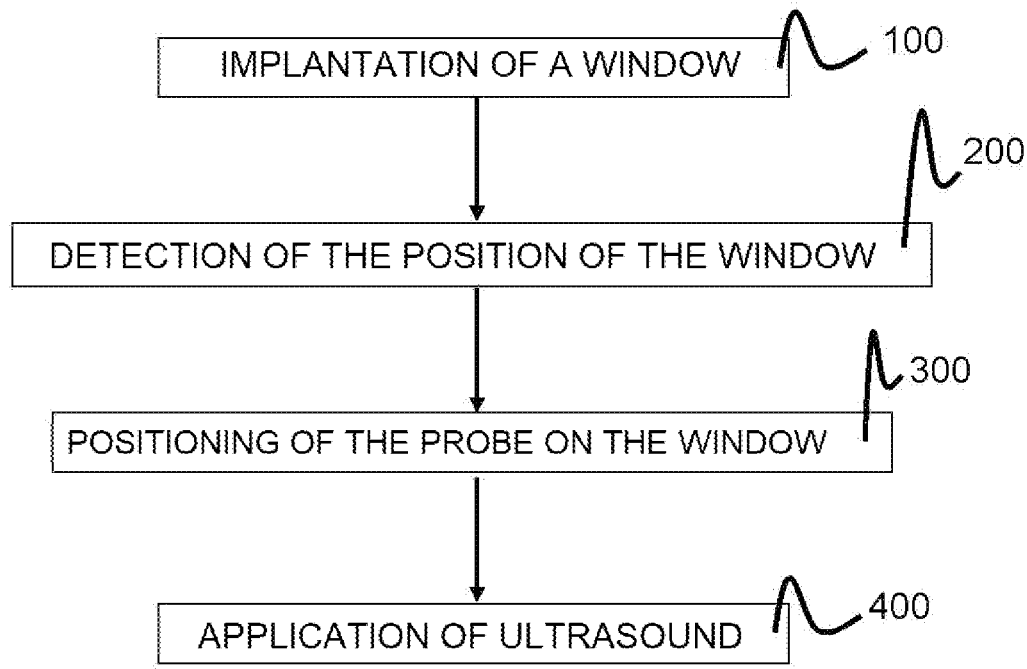
FIG. 8 is an example of a process for treating a disease using a brain tissue imaging and/or treatment system.

FIG. 7—which is a graph representing the transmission rate of ultrasound waves as a function of the angle of incidence of probe 2—illustrates the result of this experimental study.

The plates of the acoustic windows according to the invention consisted of metal meshes made of meshed wires, and having the following features:
- first acoustic window: wire diameter 250 µm, period of the mesh: 2.1 mm (ø=0.17λ, distance=1.4λ),
- second acoustic window: wire diameter 220 µm, period of the mesh: 1.25 mm (ø=0.15λ, distance=0.8λ),
- third acoustic window: wire diameter 150 µm, period of the mesh: 0.59 mm (ø=0.10λ, distance=0.4λ).

As can be seen from FIG. 7, the transmission curves 53, 54, 55 of the acoustic windows according to the invention are greater than 95% for angles of incidence comprised between 0 and 60° with respect to normal incidence N. The transmission curve 51 of the acoustic window comprising a solid PEEK plate tends towards 0 for angles of incidence greater than 20°.

6. Conclusions

The acoustic window according to the invention maximizes the transmission of the ultrasound waves generated by an ultrasound probe (transmission coefficient higher than 90%) for large angles of incidence (i.e., angle of incidence comprised between 0 and 60° with respect to normal incidence N), without deforming the ultrasound wave field.

Thus, the acoustic window according to the invention allows imaging or treatment of a maximum brain volume compared with acoustic windows including a solid plate.

The reader will have understood that a number of modifications can be made to the above-described invention without materially departing from the new teachings and advantages presented herein.

For example, the through-holes of the plate can have different shapes.

Consequently, all modifications of this type are intended to be incorporated within the scope of the appended claims.

The invention claimed is:

1. An acoustic window configured to be implanted at an opening in a patient's skull, said acoustic window cooperating with an external ultrasound probe for the emission of ultrasound waves through the acoustic window,
    wherein the acoustic window comprises:
        a plate whose stiffness is configured to satisfy a minimum deformation criterion which is that a force of 100 Newtons applied to the center of the plate must generate a deformation of less than 5 millimeters, and
        through-holes within the plate,
        wherein the plate and the through-holes satisfy the following criteria to allow the transmission of ultrasound waves at angles greater than 20° relative to an angle of incidence normal to the plate;
            a distance P between two adjacent through-holes is less than five times the wavelength of the ultrasound waves emitted by the external ultrasound probe, and
            a surface area covered by the through-holes is greater than or equal to 50% of the total surface area of the plate.

2. The acoustic window as claimed in claim 1, wherein the material constituting the plate is a material of high acoustic impedance higher than $5 \times 10^6$ Pa s/m.

3. The acoustic window as claimed in claim 1, wherein the distance P between two adjacent through-holes is less than twice the wavelength of the ultrasound waves emitted by the external ultrasound probe.

4. The acoustic window as claimed in claim 3, wherein the distance P between two adjacent through-holes is less than 1.7 times the wavelength of the ultrasound waves emitted by the external ultrasound probe.

5. The acoustic window as claimed in claim 4, wherein the distance P between two adjacent through-holes is less than the wavelength of the ultrasound waves emitted by the external ultrasound probe.

6. The acoustic window as claimed in claim 1, wherein a dimension D of each through-hole is less than twice the wavelength of the ultrasound waves emitted by the external ultrasound probe.

7. The acoustic window as claimed in claim 6, wherein the dimension D of each through-hole is less than 1.7 times the wavelength of the ultrasound waves emitted by the external ultrasound probe.

8. The acoustic window as claimed in claim 7, wherein the dimension D of each through-hole is less than the wavelength of the ultrasound waves emitted by the external ultrasound probe.

9. The acoustic window as claimed in claim 1, wherein the through-holes are identical in shape.

10. The acoustic window as claimed in claim 1, wherein the through-holes are evenly distributed over the plate.

11. The acoustic window as claimed in claim 1, wherein the through-holes are arranged in a square arrangement.

12. The acoustic window as claimed in claim 1, wherein the through-holes are arranged in a hexagonal arrangement.

13. The acoustic window as claimed in claim 1, which further comprises at least one layer of polymeric material containing the plate.

14. The acoustic window as claimed in claim 1, which further comprises at least one positioning marker.

15. The acoustic window as claimed in claim 1, which further comprises a reinforcing frame extending around a periphery of the plate.

16. The acoustic window as claimed in claim 1, wherein the surface area covered by the through-holes is greater than or equal to 75% of the total surface area of the plate.

17. The acoustic window as claimed in claim 16, wherein the surface area covered by the through-holes is greater than or equal to 90% of the total surface area of the plate.

18. A surgical implant set comprising a package, wherein the implant set comprises a window contained in the package, and instructions for use of the window as an acoustic window configured to be implanted at an opening in a patient's skull, said acoustic window cooperating with an external ultrasound probe for the emission of ultrasound waves through the acoustic window, wherein the acoustic window comprises:
- a plate whose stiffness is configured to satisfy a minimum deformation criterion which is that a force of 100 Newtons applied to the center of the plate must generate a deformation of less than 5 millimeters, and through-holes within the plate,
  - wherein the plate and the through-holes satisfy the following criteria to allow the transmission of ultrasound waves at angles greater than 20° relative to an angle of incidence normal to the plate;
  - a distance P between two adjacent through-holes is less than five times the wavelength of the ultrasound waves emitted by the external ultrasound probe, and
  - a surface area covered by the through-holes is greater than or equal to 50% of the total surface area of the plate.

19. A system for imaging and/or treating brain tissue, the system including an ultrasound-wave-generating probe, wherein the system further comprises an acoustic window configured to be implanted at an opening in a patient's skull, said acoustic window cooperating with the ultrasound-wave-generating probe for the emission of ultrasound waves through the acoustic window, wherein the acoustic window comprises:
- a plate whose stiffness is configured to satisfy a minimum deformation criterion which is that a force of 100 Newtons applied to the center of the plate must generate a deformation of less than 5 millimeters, and through-holes within the plate,
- wherein the plate and the through-holes satisfy the following criteria to allow the transmission of ultrasound waves at angles greater than 20° relative to an angle of incidence normal to the plate;
- a distance P between two adjacent through-holes is less than five times the wavelength of the ultrasound waves emitted by the ultrasound-wave-generating probe,
- a surface area covered by the through-holes is greater than or equal to 50% of the total surface area of the plate.

20. The system for imaging and/or treating brain tissue according to claim 19, wherein the material constituting the plate is a material of high acoustic impedance higher than $5 \times 10^6$ Pa s/m.

21. The system for imaging and/or treating brain tissue according to claim 19, wherein the distance P between two adjacent through-holes is less than twice the wavelength of the ultrasound waves emitted by the ultrasound-wave-generating probe.

22. The system for imaging and/or treating brain tissue according to claim 21, wherein the distance P between two adjacent through-holes is less than 1.7 times the wavelength of the ultrasound waves emitted by the ultrasound-wave-generating probe.

23. The system for imaging and/or treating brain tissue according to claim 22, wherein the distance P between two adjacent through-holes is less than the wavelength of the ultrasound waves emitted by the ultrasound-wave-generating probe.

24. The system for imaging and/or treating brain tissue according to claim 19, wherein a dimension D of each through-hole is less than twice the wavelength of the ultrasound waves emitted by the ultrasound-wave-generating probe.

25. The system for imaging and/or treating brain tissue according to claim 24, wherein the dimension D of each through-hole is less than 1.7 times the wavelength of the ultrasound waves emitted by the ultrasound-wave-generating probe.

26. The system for imaging and/or treating brain tissue according to claim 25, wherein the dimension D of each through-hole is less than the wavelength of the ultrasound waves emitted by the ultrasound-wave-generating probe.

27. The system for imaging and/or treating brain tissue according to claim 19, wherein the through-holes are identical in shape.

28. The system for imaging and/or treating brain tissue according to claim 19, wherein the through-holes are evenly distributed over the plate.

29. The system for imaging and/or treating brain tissue according to claim 19, wherein the through-holes are arranged in a square arrangement.

30. The system for imaging and/or treating brain tissue according to claim 19, wherein the through-holes are arranged in a hexagonal arrangement.

31. The system for imaging and/or treating brain tissue according to claim 19, which further comprises at least one layer of polymeric material containing the plate.

32. The system for imaging and/or treating brain tissue according to claim 19, which further comprises at least one positioning marker.

33. The system for imaging and/or treating brain tissue according to claim 19, which further comprises a reinforcing frame extending around a periphery of the plate.

34. The system for imaging and/or treating brain tissue according to claim 19, wherein the surface area covered by the through-holes is greater than or equal to 75% of the total surface area of the plate.

35. The system for imaging and/or treating brain tissue according to claim 34, wherein the surface area covered by the through-holes is greater than or equal to 90% of the total surface area of the plate.

* * * * *